US00PP10622P

United States Patent [19]

Meilland

[11] Patent Number: Plant 10,622

[45] Date of Patent: Sep. 29, 1998

[54] HYBRID TEA ROSE PLANT NAMED 'MEICOBUIS'

[75] Inventor: Alain A. Meilland, Antibes, France

[73] Assignee: CP (Delaware), Inc., Wilmington, Del.

[21] Appl. No.: 904,439

[22] Filed: Jul. 31, 1997

[51] Int. Cl.[6] ..... A01H 5/00

[52] U.S. Cl. ..... Plt./17

[58] Field of Search ..... Plt./16, 17, 19, Plt./20, 11

[56] References Cited

U.S. PATENT DOCUMENTS

P.P. 9,997 8/1997 Meilland ..... Plt./11

*Primary Examiner*—Howard J. Locker

*Attorney, Agent, or Firm*—Burns, Doane, Swecker & Mathis, L.L.P.

[57] ABSTRACT

A new and distinct variety of Hybrid Tea rose plant is provided that is a mutation of the 'Meicofum' variety (U.S. Plant Pat. No. 9,997) of unknown causation. Unlike the parent the new variety forms large double blossoms that are an attractive Brick Red on both surfaces. The blossoms are long lasting when cut and placed in a vase. The growth habit is erect. Dense and semi-glossy foliage is formed. The new variety is particularly well suited for cut flower production under greenhouse growing conditions.

1 Drawing Sheet

SUMMARY OF THE INVENTION

The new variety of Hybrid Tea rose plant was discovered during 1994 at Le Cannet des Maures, Var, France while growing among plants of the 'Meicofum' variety (U.S. Plant Pat. No. 9,997). The new variety of the present invention is believed to be a mutation of the 'Meicofum' variety of unknown causation. The new variety was selected and preserved primarily because of its distinctive blossom coloration that differed from that of the parent 'Meicofum' variety. More specifically, the 'Meicofum' parent exhibits bicolored blossoms that are reddish orange on the upper surface and creamy yellow on the under surface, and the blossom coloration of the new variety is substantially the same on both surfaces. Had the single plant of the new variety not been discovered and preserved it would have been lost to mankind.

It was found that the new variety of Hybrid Tea rose plant of the present invention possesses the following combination of characteristics:

(a) forms in abundance attractive long lasting large double blossoms that are Brick Red on both surfaces,
(b) exhibits an erect growth habit,
(c) forms dense semi-glossy foliage, and
(d) is particularly well suited for cut flower production under greenhouse growing conditions.

The new variety well meets the needs of the horticultural industry and can be used to advantage during the commercial production of cut flowers.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Meicobus' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during November while budded on *Rosa indicia* understock and growing indoors at Le Cannet des Maures, Var, France. Dimensions in centimeters are indicated at the bottom of the photograph.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a leaf with three leaflets—plan view—upper surface; and FIG. 14—illustrates a specimen of a leaf with five leaflets—plan view—under surface.

DETAILED DESCRIPTION

Figures 1, 2, 3, 4, 5, 6, 7, 8, 9, 10, 11, 12, 13:
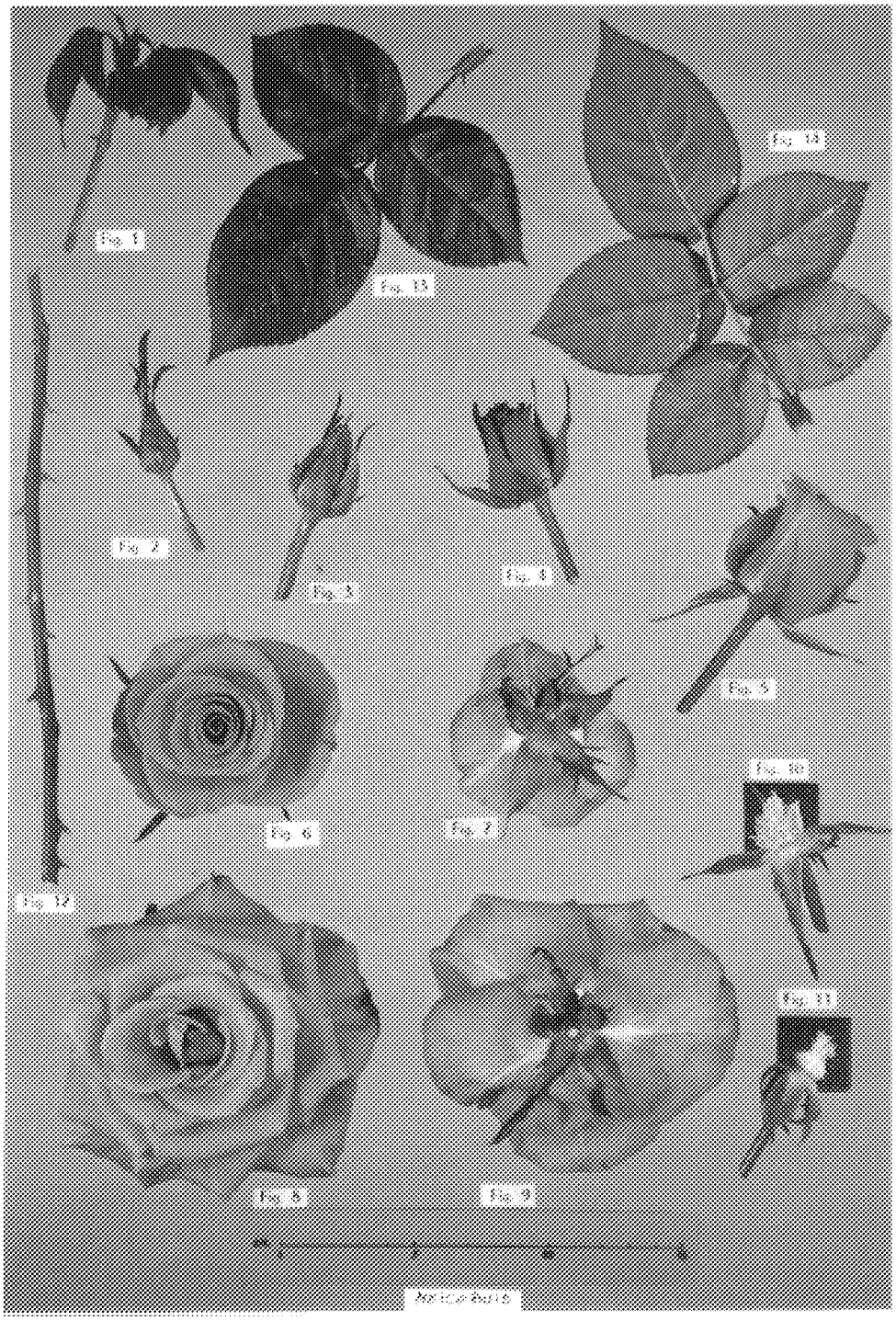

The chart used in the identification of the colors is that of The Royal Horticultural Society (R.H.S. Colour Chart). The description is based on the observation of two year-old plants during November while budded on *Rosa indica* understock and growing indoors at Le Cannet des Maures, Var, France. The coloration in common terms precedes reference to the chart in some instances.

Class: Hybrid Tea.

Plant:

*Height.*—When pruned to a height of 0.85 cm., floral stems having a length of approximately 50 to 70 cm. commonly are produced at the end of the growing season.

*Habit.*—Erect.

Branches:

*Color.*—Young stems: light green, Green Group 139C, and lightly suffused with reddish brown. Adult wood: medium green, Green Group 137D.

*Thorns.*—Size: medium. Quantity: moderately numerous. Color: greenish-red on young stems and greenish (near Yellow-Green Group 144D) changing to tan on adult wood.

Leaves:

*Stipules.*—Adnate, pectinate, narrow and linear.

*Petioles.*—Upper surface: striped reddish brown on young foliage, and medium green (near Green Group 137C) on adult foliage. Under surface: light green and rarely bear some small thorns.

*Leaflets.*—Number: 3, 5 (most often), and 7. Shape: oval. Serration: simple and regular (as illustrated). Texture: consistent. General appearance: dense and semi-glossy. Color (young foliage): upper surface: bronze green, Yellow-Green Group 146A, and suffused with reddish brown. under surface: light Greyed-Green Group 191B, and suffused with reddish brown. Color (adult foliage): upper surface: medium green, Green Group 137A. under surface: light green, Green Group 138B.

Inflorescence:

*Number of flowers.*—Usually one per stem.

*Peduncle.*—Light green (near Green Group 142B), smooth, and the length is approximately 12 to 13 cm. on average.

*Sepals.*—Upper surface: tomentose, and greenish (near Green Group 143C) in coloration. Under surface: light green commonly with a few small extensions.

*Buds.*—Shape: conical. Length: approximately 4 cm. on average. Size: medium. Color upon opening: upper surface: near Orange Brick, Greyed-Orange Group 171B and Greyed-Orange Group 169B. under surface: near Orange Brick, Greyed-Orange Group 171B and Greyed-Orange Group 169B.

*Flower.*—Shape: cupped with a high center. Diameter: approximately 12 to 14 cm. on average. Color (when opening begins): upper surface: Orange Red, Orange Red Group 34B. under surface: Orange Red, Orange Red Group 34C. Color (when blooming): upper surface: near Brick Red, Orange-Red Group 35B and Orange-Red Group 34C. under surface: Brick Red, Orange-Red Group 35B. Color (at end of opening): upper surface: Brick Red, Orange-Red Group 35B. under surface: Brick Red, Orange-Red Group 35B. Fragrance: none. Lasting quality: long (e.g., approximately 8 days on average) when cut and placed in a vase. Petal shape: rounded with reflexed edges (as illustrated). Petal number: approximately 22 to 25 on average. Stamen number: approximately 82 to 90 on average. Anthers: near Yellow Group 4B in coloration. Filaments: Canary Yellow in coloration. Pistil number: approximately 75 to 80 on average. Stigmas: near Yellow Group 9A in coloration. Styles: Canary Yellow (near Yellow Group 4D) in coloration. Receptacle: light green (near Green Group 142B), smooth, and in longitudinal section in the shape of a funnel.

Development:

*Vegetation.*—Moderately strong.

*Blooming.*—Abundant. When grown under greenhouse conditions approximately 190 bossoms commonly are formed per square meter per year.

*Resistance to diseases and pests.*—Good with respect to downy mildew and thrips, and fair with respect to powderly mildew, botrytis, aphids and red spider mites.

I claim:

1. A new and distinct variety of Hybrid Tea rose plant characterized by the following combination of characteristics:

(a) forms in abundance attractive long lasting large double blossoms that are Brick Red on both surfaces,
(b) exhibits an erect growth habit,
(c) forms dense semi-glossy foliage, and
(d) is particularly well suited for cut flower production under greenhouse growing conditions;

substantially as herein shown and described.

* * * * *